United States Patent [19]

Byers

[11] E Patent Number: Re. 33,170

[45] Reissued Date of Patent: Feb. 27, 1990

[54] SURGICALLY IMPLANTABLE DISCONNECT DEVICE

[75] Inventor: Charles L. Byers, Vacaville, Calif.

[73] Assignee: The Regents of the University of California, Berkeley, Calif.

[21] Appl. No.: 811,019

[22] Filed: Dec. 18, 1985

Related U.S. Patent Documents

Reissue of:

[64] Patent No.: 4,495,917
Issued: Jan. 29, 1985
Appl. No.: 362,344
Filed: Mar. 26, 1982

[51] Int. Cl.[4] ..... A61N 1/04

[52] U.S. Cl. ..... 128/419 R; 128/784; 128/903

[58] Field of Search ..... 128/419 P, 419 R, 419 F, 128/419 G, 746, 642, 419 PG, 903; 179/107 R, 107 BC, 107 FD; 3/1; 339/116 C, 17 F

[56] References Cited

U.S. PATENT DOCUMENTS

| | | | |
|---|---|---|---|
| 3,478,297 | 11/1969 | Gimpel et al. | 339/60 B |
| 3,657,681 | 4/1972 | Falkner | 339/61 M |
| 3,701,964 | 10/1972 | Cronin | 339/17 F |
| 3,731,258 | 5/1973 | Spicer | 339/48 |
| 3,995,644 | 12/1976 | Parsons | 128/784 |
| 4,054,479 | 10/1977 | Pieffer | 156/280 |
| 4,116,517 | 9/1978 | Selvin et al. | 339/17 F |
| 4,125,310 | 11/1978 | Reardon et al. | 339/17 F |
| 4,162,226 | 7/1979 | Lehmann | 430/169 |
| 4,221,444 | 9/1980 | Patrick | 335/17 M |
| 4,229,616 | 10/1980 | Hotchkiss | 339/116 T |
| 4,255,003 | 3/1981 | Berg | 339/17 LN |
| 4,311,137 | 1/1982 | Gerard | 604/28 |
| 4,361,153 | 11/1982 | Slocum et al. | 128/903 |
| 4,400,590 | 8/1983 | Michelson | 179/107 FD |

OTHER PUBLICATIONS

"Electrocardial RF Pacemaker"; Barr et al, 5-67.
"Bone Plating", Down Bros. et al.
"Gold Dot—A Non-Connector . . . ", Wittmann, Hughes Aircraft Co.
"Metal-Elastomeric Display Connectors", L. S. Buchoff, Proceedings of SID, vol. 21/2, 1980.
"Recent Developments . . . ", C. L. Byers.
"Cochlear Implant Prostheses: Strategies and Progress", Merzenich et al, 6-5-81, Pergamon Press.

*Primary Examiner*—Edward M. Coven
*Attorney, Agent, or Firm*—Phillips, Moore, Lempio & Finley

[57] ABSTRACT

A surgically implantable connector for a transcutaneous driving system comprised of a case having a base and a lid which are shaped to provide a cavity between them with a first elastomeric pad for supporting a first set of electrical contacts in the cavity which contacts mate with a second set of electrical contacts carried by the lid, a second elastomeric pad for supporting a third set of electrical contacts inbetween the lid and the first pad and which mate with the first or the second set of electrical contacts, means for electrically connecting the firs set of electrical contacts to an implantable electrode, means for electrically connecting the second set of electrical contacts to the driving system and means for electrically connecting the third set of electrical contacts to a percutaneous plug.

23 Claims, 5 Drawing Sheets

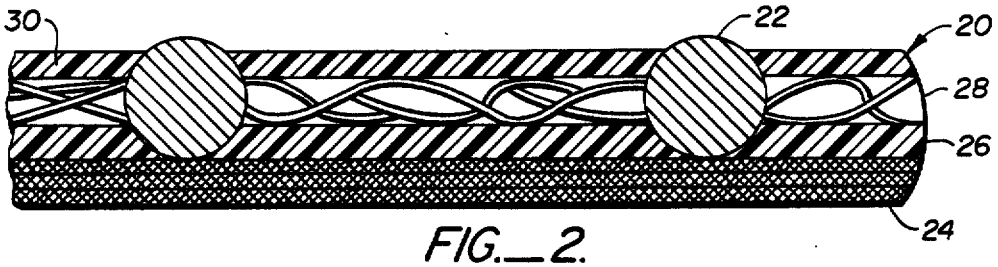
FIG._2.
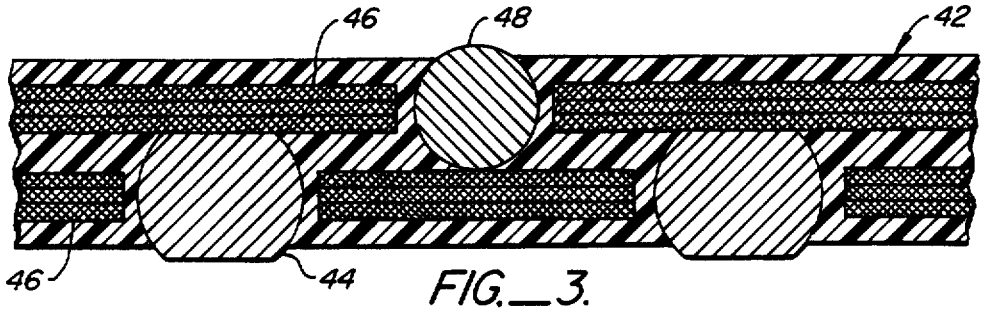
FIG._3.
FIG._4A.
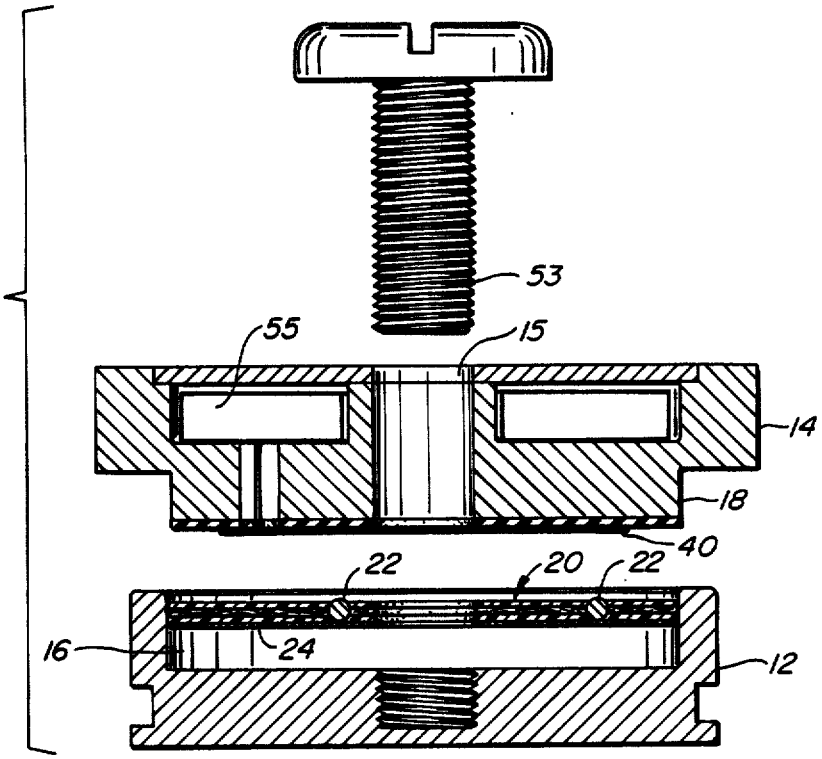

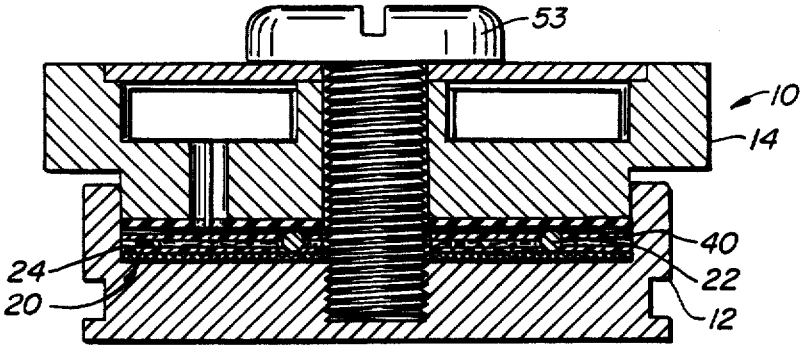
FIG._4B.
FIG._5A.
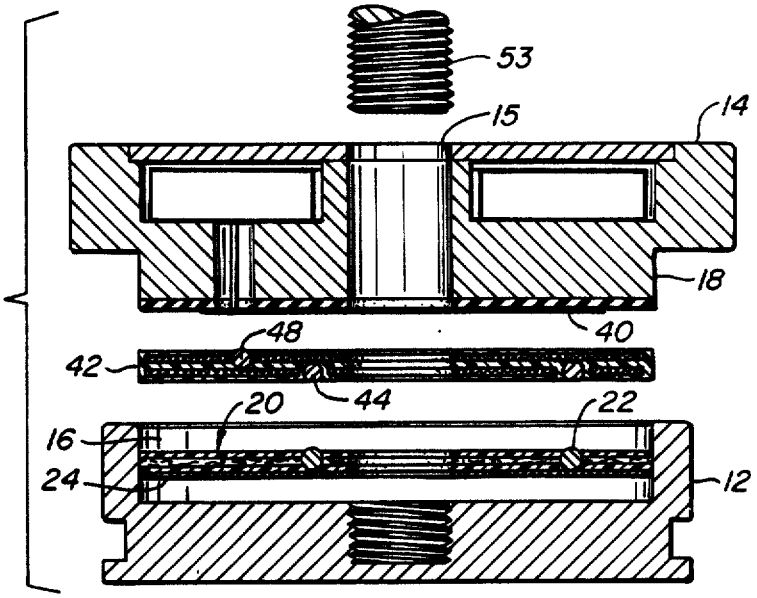
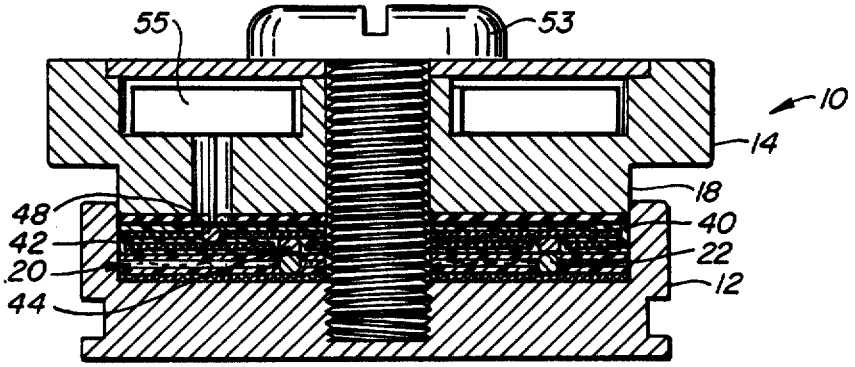
FIG._5B.

SURGICALLY IMPLANTABLE DISCONNECT DEVICE

Matter enclosed in heavy brackets [ ] appears in the original patent but forms no part of this reissue specification; matter printed in italics indicates the additions made by reissue.

The invention described herein was made in the course of work under a grant or award from the Department of Health and Human Services.

BACKGROUND OF THE INVENTION

This invention relates to an electrical connector and more particularly one for use in the human body.

In cochlear stimulating prostheses systems an electrical connector is often placed between the stimulating electrode and the driving component of the prosthesis to allow the driving component to be removed, replaced, or converted to another driving system, without disturbing the electrode itself. This connection and disconnection can be done by either mounting the connector in a channel through the skin (referred to as a percutaneous plug) or by implanting the connector beneath the skin (referred to as a surgical disconnect).

Percutaneous plugs seem to have a limited rather than a permanent life span of usefulness due to the ever present threat of infection through the open skin, and a tendency of the epithelium to bridge beneath such a foreign body and to eject it. Further, a percutaneous plug will usually never be considered in a transcutaneous driving system which emphasizes a fully implanted radio frequency or ultra sonic receiver. In such systems the receiver is implanted under the skin and receives signals from a transmitter located outside of the human body. The transmitter is of course, connected to a transducer and amplifier to convert audio signals into either radio signals or ultra sonic signals which are transmitted through the patient's skin to be detected by a receiver or a transducer connected to an amplifier within the patient's body.

From an engineering standpoint, the surgical disconnect presents unique problems. It must be small yet still easily manipulated by a gloved surgeon. It must be rugged, biologically inert, and should function reliably in a very hostile environment through multiple disconnection and reconnection cycles. For multi-channel systems it must carry fifteen to twenty leads or more.

Pin-type connectors have been succesfully adapted in prior art surgical disconnects for cochlear implant systems. There are, however, some disadvantages with such pin-type connectors. Such connectors involve the use of non-biocompatible metal like beryllium copper. Such copper pins are isolated by gold plate in the expoxy connector housing but some small risk remains. The need to weld or solder the leads to the electrode also adds a potential failure site to the device. And finally, there is a constant desire to reduce the size of any implant.

Still another serious problem is to electrically isolate each of the contacts in the disconnect and prevent water vapor or liquid from causing a short circuit between them.

SUMMARY OF THE INVENTION

The above and other disadvantages of prior art implantable connectors are overcome by the present invention of a connector comprising a case, including a base member and a lid which are shaped to form a cavity between them, a first contact pad of elastomeric material, a first set of electrical contacts imbedded in the first contact pad, and with the first contact pad being dimensioned to fit within the cavity. Either the lid or the base member has a portion which is dimensioned to fit within the cavity. The lid has a second set of electrical contacts which are located on one wall of the cavity. Separate electrical connections are made through the case to the first and second sets of electrical contacts.

Means are provided in the form of a screw for pressing the lid against the base member and the contact pad to exert a predetermined pressure on the pad, thereby causing it to form a fluid tight seal around the first and second sets of electrical contacts, some of which are thereby placed in electrical contact with each other. The first set of electrical contacts are electrically connected to the intra-cochlear electrode. The second set of electrical contacts are connected to the driving system which, in the preferred embodiment, is housed in the case lid.

In the preferred embodiment a second contact pad is also provided which has a third set of electrical contacts arranged in a pattern to mate with the first set of electrical contacts. The second contact pad is also made of elastomeric material and is dimensioned to fit within the cavity. The third set of electrical contacts are connected through the case to a percutaneous connector. This second contact pad is interposed between the first contact pad and the lid so that when the lid and base member are forced together the third set of electrical contacts will be placed against the first set of electrical contacts. A fluid tight seal is thereby effected between the first and third sets of electrical contacts, some of which are also electrically connected together.

There are several advantages to the contact pad approach. By the configuration of the first, second, and third electrical contacts any combination of connections between the individual electrodes can be made. Furthermore the combination of electrodes can be relatively easily changed by simply changing the lid of the disconnect or by changing the contact pads.

In the embodiment in which a second contact pad is provided, patient testing can now be done in a form which was not previously possible. This second or interface pad carries leads to and from a percutaneous plug through which multi-channel information can be input and both the electrode array and the driving system can be monitored. This plug need only be utilized by the research staff in the hospital facility conducting the tests. While away from the facility the patient wears a radio frequency or ultra sonic transmitter connected to an audio transducer and amplifier system. Thus the risk of damage to the plug or infection at the side is reduced through reduced and closely monitored handling of the percutaneous plug. Also, the percutaneous plug site is sufficiently distant from the implanted disconnect that any infection there would not threaten the implanted connector site. At the end of the test series or at the first indications of infection the percutaneous plug can be removed along with its electrical contact pad and the patient will retain the transcutaneous driving system. If indicated by the test series, the lid and the receiving unit in it can be replaced with one which is reconfigured to stimulate a more optimal combination of electrodes.

It is therefore an object of the present invention to provide an implantable disconnect which provides an easily manipulated fluid tight seal between electrical contacts.

It is still another object of the invention to provide an implantable disconnect made of biocompatible materials.

It is still another object of the invention to provide a disconnect which allows easy interconnections between an implanted electronic driving circuit, a percutaneous connector and an implanted electrode.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIG. 2 is an enlarged, vertical, sectional view of a first electrical contact pad taken generally along the line 2—2 in FIG. 1;

FIG. 3 is an enlarged, vertical, sectional view of an interface electrical contact pad taken generally along the line 3—3 in FIG. 1;

FIGS. 4a and 4b are enlarged vertical, sectional views illustrating one method of assembly of the embodiment depicted in FIG. 1;

FIGS. 5a and 5b are enlarged vertical, sectional views illustrating a second method of assembly of the embodiment depicted in FIG. 1 when an interface pad is utilized;

DETAILED DESCRIPTION OF CERTAIN PREFERRED EMBODIMENTS

Figure 1:
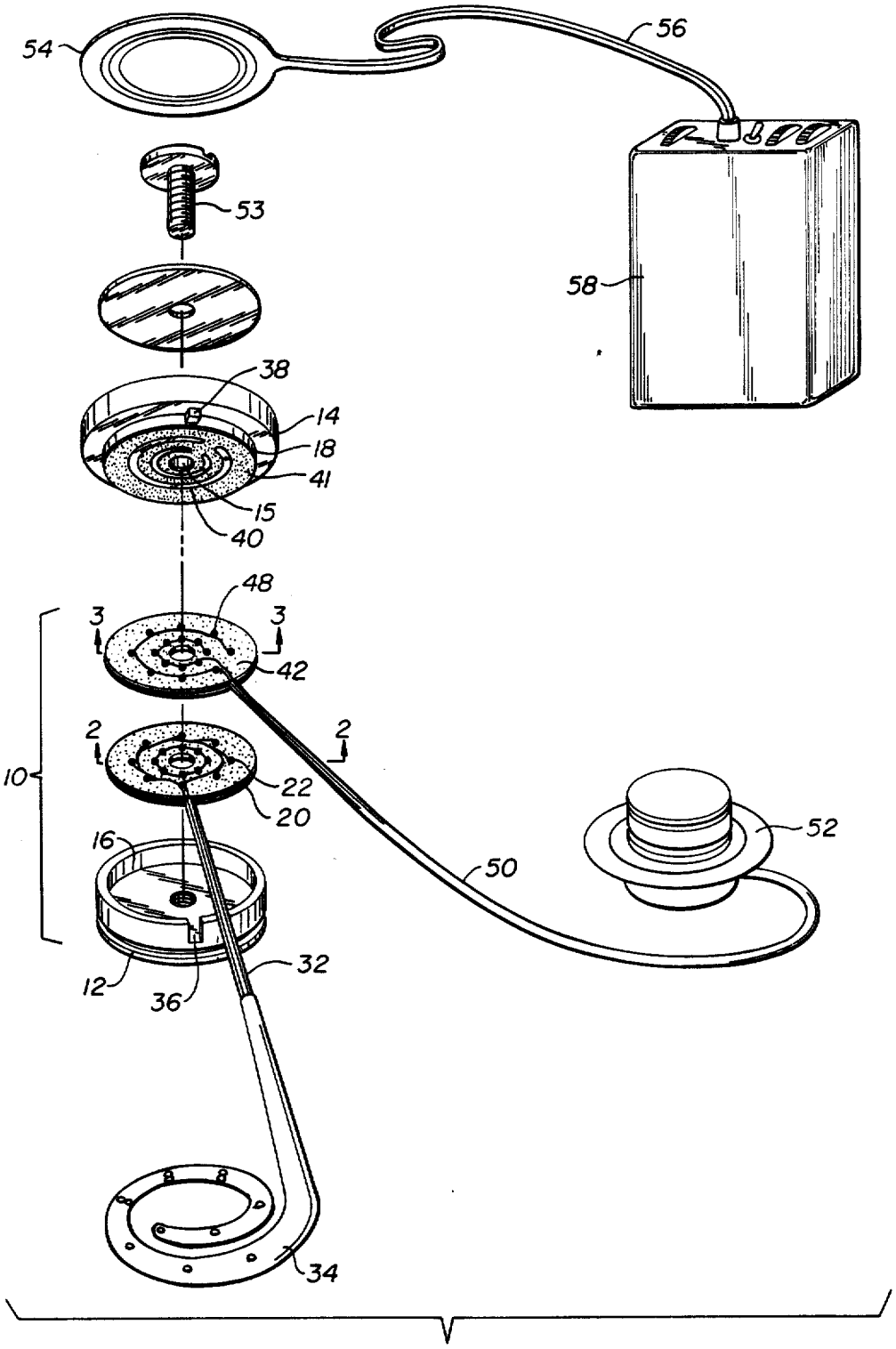
FIG. 1 is an exploded, perspective view of a surgical disconnect according to one embodiment of the invention together with the components of a cochlear stimulating prosthesis.

Referring now more particularly to FIG. 1 an implantable disconnect 10 according to the invention is illustrated in exploded form. The disconnect is comprised of a casing made up of a hollow base member 12 and a lid 14. The base member 12 is in the form of a cylinder and has a cavity 16 therein. The base member 12 is intended to be cemented into a surgically created recess in a bone of the patient, such as the skull. Lid 14 is also in the form of a cylinder and has a reduced diameter section 18 which is dimensioned to fit within the cavity 16 of the base member 12. The lid and the base member are made of a biocompatible material such as titanium.

A first electrical contact pad 20, made of elastomeric material is dimensioned to fit within the cavity 16. The pad 20 carries a first set of electrical contacts 22 embedded in it. The contacts are arranged in a radial pattern about a hypothetical axis of revolution which passes through the entire disconnect 10.

Referring more particularly to FIG. 2 it can be seen that the pad 20 is made of a silicone rubber material reinforced with a first layer of fine dacron mesh 24 followed by an unreinforced layer of silicone rubber 26 and then followed by a second dacron mesh layer 28 which is more loosely woven than the layer 24. Finally an unreinforced layer 30 is the topmost layer as viewed in FIG. 2.

The contacts 22 are formed by melting the free ends of platinum-iridium wires to form essentially uniform spheres. These spheres are then embedded in the matrix of silicone rubber reinforced mesh of the pad 20 in a radially spaced pattern. The other ends of the wires are gathered together to form a cable 32 which connects the first set of contacts 22 to an intracochlear electrode 34. Thus there are no welds or solder joints needed to connect the cable wires to the contacts of the disconnect.

The cable 32 passes through an aperture 36 in the base member 12 so that the pad 20 and contacts 22 assume a fixed orientation with respect to the lid 14 and base member 12. The lid 14 is aligned with the base 12 and the pad 20 by a protrusion 38 on the lid 14 which mates with the aperture 36.

A second set of electrical contacts 40 is positioned on a layer of elastomeric material 41 on the underside of the reduced diameter section 18 of the lid 14. These contacts are arranged in a pattern to mate with some or all of the first set of contacts 22, as will be described in greater detail hereinafter.

An interface contact pad 42, which is also dimensioned to fit within the cavity 16, is positioned between the first pad 20 and the reduced diameter section 18 of the lid 14. The pad 42 is also constructed of an elastomeric material such as silicone rubber and carries a third set of electrical contacts 44 (not shown in FIG. 1) which protrude from the underside of the pad 42 as viewed in FIG. 1.

As is more clearly shown in FIG. 3, these contacts 44 are also melted balls on the ends of platinum-iridium wires which have been flattened slightly to ensure good contact with complementary contacts 22 of the pad 20. The contacts 44 are arranged in a radial pattern about the hypothetical axis of revolution of the disconnect 10 and are embedded in the pad 42. The pad 42 is comprised of a layer of silicone rubber with intermediate layers of fine dacron mesh 46. The interface pad also carries a fourth set of electrical contacts 48 on its upper surface as viewed in FIGS. 1 and 3. The contacts 48 are also arranged in a radial pattern about the hypothetical axis of revolution and, like and contacts 44 and 22, are formed by melting the ends of platinum-iridium wires to form spheres of uniform diameter.

The contacts 44 are arranged in a pattern to mate with some or all of the contacts 22 of pad 20. The contacts 48 are arranged to mate with some or all of the contacts 40 of the lid 14. All of the contacts 44 and 48 are separately connected by means of a cable bundle 50 of platinum-iridium wires to a percutaneous plug 52.

The entire assembly 10 is held together by means of a screw 53 which passes through a hole 15 in the lid 14 along the hypothetical axis of revolution and threadably engages in the base member 12. When the screw 53 is tightened the lid 14 is pressed down on the pads 42 and 20 to cause them to deform, the electrical contacts to mate, and the elastomeric material on the layer 41 and the pads 20 and 42 to form fluid tight seals around the contacts 22,44 and 48.

The lid 14 is hollow and contains a receiver/driver circuit 55 (shown in FIG. 4A). In the preferred embodiment the receiver/driver 55 is part of a transcutaneous driving system of a cochlear stimulating prostheses. The entire disconnect 10 along with the receiver/driver 55 is positioned near the surface of the skin so that when the antenna or ultrasonic transducer 54, which is connected via a cable 56 to a transmitter unit 58 is placed over the disconnect 10 on the surface of the skin, the receiver/-driver 55 will detect the appropriate signal and convert it into electrical signals which are transmitted through the contacts 40, 48, 44 and 22 to the intracochlear electrode 34. At this point it should be mentioned that the disconnect 10 is also intended to operate without the presence of the second contact pad 42 as will be explained in greater detail hereinafter. In such cases the electrical signals would be transmitted directly from the contacts 40 to the contacts 22.

In the embodiment depicted in FIG. 1, however, which illustrates the research mode of the disconnect 10, the signals derived from the contacts 40 pass through the cable 50 to the percutaneous connector 52. They can then be monitored by researchers through the connector 52 or, in other cases, the signals can be directed back through the cable 50 via connections made at the plug 52 to pass on through the contacts 44 and 22 to the intracochlear electrode 34. Thus the researcher can control what connections are made to the intracochlear electrode as well as monitor the signals through the percutaneous connector 52.

While the patient is away from the research facility he or she relies solely on the transmitter 58; the plug 52 would not be utilized or handled. Thus the risk of damage to the plug or infection at that site is reduced through reduced and closely monitored handling of the plug 52. Also the plug site 52 is sufficiently distant from the site of the disconnect 10 that any infection at the plug site would not threaten the connector site. At the end of the test series or at the first indications of infection, the percutaneous plug 52 can be surgically removed along with its interface pad 42 and the patient will then retain the transcutaneous driving system. Also, if indicated by the test series, the lid 14 along with the transcutaneous receiver therein, could be replaced with one which is reconfigured to stimulate a more optimal combination of electrodes in the intracochlear electrode 34.

Referring now more particularly to FIGS. 4a and 4b the assembly of the disconnect 10 is shown when the interface pad 42 is removed. Under these circumstances the electrical contacts 40 mate directly with the first set of contacts 22 when the screw 53 is threadably engaged in the base member 12 to clamp the lid 14 down against the pad 20.

Referring now more particularly to FIGS. 5a and 5b the assembly of the disconnect 10 is illustrated when the interface pad 42 is present. Under these circumstances the contacts 40 only mate with the contacts 48 and the contacts 44 of the interface pad mate with the contacts 22 of the first contact pad. In both cases the tightening of the screw 53 in the base member 12 causes the lid 14 to press the pads 20 and 42 against the base member 12 with a predetermined pressure sufficient to effect the fluid tight seal among the various electrical contacts.

Figure 6:
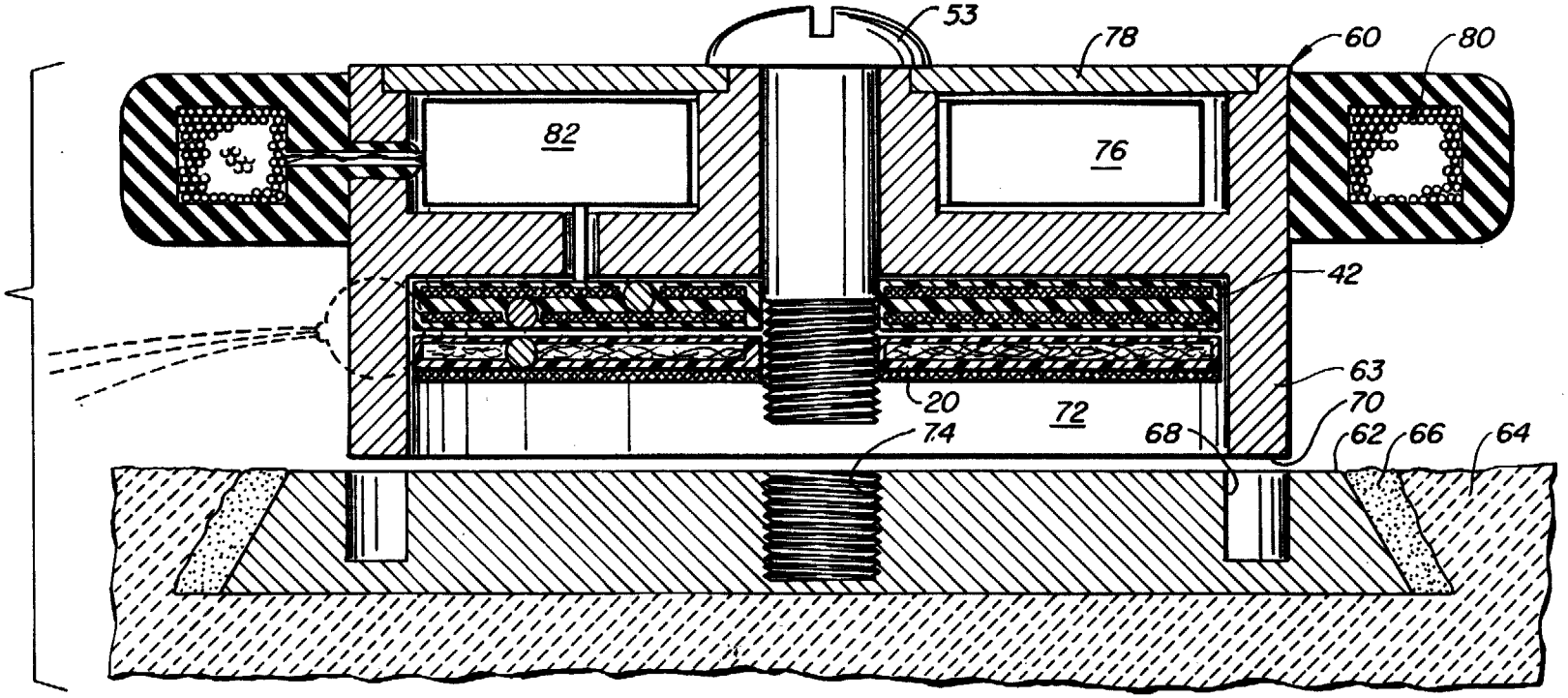
FIG. 6 is an enlarged, vertical, sectional view of a second embodiment of the invention.

Referring now more particularly to FIG. 6 an alternative embodiment of the invention is illustrated. In this embodiment a disconnect 60 is made of a base member 62 and a lid 63. The base member 62 is essentially a flat plate with sloping side edges which is cemented in a surgically created cavity in the bone 64 of a patient by means of a surgical adhesive or cement 66. The base member 62 is provided with a groove 68 which receives the bottom edge 70 of the lid 63. The lid 63 is constructed to have the shape of an H in vertical cross-section to thereby create a cavity 72 between the lid 70 and the base 62.

It is into this cavity 72 that the electrical contact pads 20 and 42 are placed in the same manner as in the embodiment of FIG. 1. Similarly the second set of electrical contacts 40 are placed on the bottom surface of the lid 70, that is at the top of the cavity 72 to mate with the electrical contacts 48 or 22, depending on whether the second contact pad 42 is in place.

The screw 53 is threadably received in a recess 74 in the base member 62 to hold the lid 70 against the base member 62 and to exert the predetermined pressure on the pads 20 and 42 as in the embodiment in FIG. 1. The groove 68 is of sufficient depth to allow such pressure to be exerted by the screw 53.

The upper portion of the lid 70 contains a second cavity 76 into which the electronic receiving circuitry is installed. This cavity 76 is covered by a second lid 78 which can be cemented in a sealed relationship to the lid 70 to make a fluid tight seal. An antenna coil 80 can be mounted around the outside upper edge of the lid 70 and connected through the lid to electronic circuitry 82 within the cavity 76. The disconnect 60 is preferably cylindrical however it can take other shapes in other embodiments.

Figure 7:
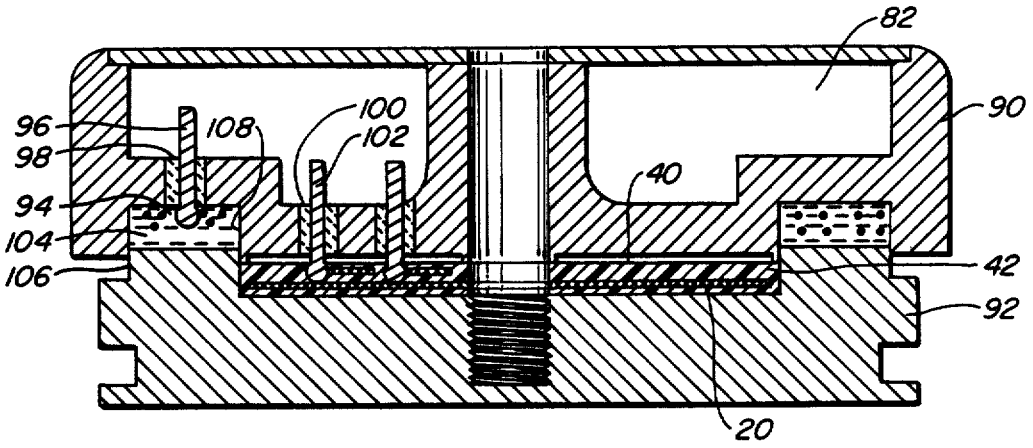
FIG. 7 is an enlarged, vertical, sectional view of a third embodiment of the invention.

Referring now more particularly to FIG. 7, still another embodiment of the invention is illustrated. In this embodiment the junction of the antennae coil wires to the input feedthroughs to the electronics receivers is sealed in the same manner as the electrical contacts in the contact pads. It has been found that potting around the weld site with an elastomer is not sufficient, since the water vapor, which can pass through the elastomer, condenses on the weld (or solder) joint. When the elastomer is placed under pressure, however, it will prevent condensation as long as the matrix is reasonably free of voids. In this embodiment, the elastomer potted around the input feedthroughs is put under pressure by the side walls of the connector base when the connector is closed.

Thus, the disconnect depicted in FIG. 7 comprises a base member 92 and lid member 90. The base member 92 is provided with a cavity portion which houses the pads 20, 40 and 42 as in the embodiments previously discussed herein. The lid 90 is provided with a cavity which contains the electronics 82 for the receiver. The electronics 82 are connected by means of feedthrough contacts 102, sealed by elastomeric potting material 100 in the bottom of the lid 90, to contact the pads 42 as in the previously described embodiments.

The base member 92 is also provided with a circumferential ridge 106 which mates with a corresponding circumferential groove 108 in the lid 90. Within the groove 108 is placed the antennae coil 94. It is connected by means of the feedthrough 96 to the electronics 82. The antennae 94 is potted in an elastomeric material 104 of the type previously described. When a bolt (not shown) is passed through the lid 90 and screwed into the base 92, thereby forcing the lid 90 down on to the base 92, the contact pad 42 and the elastomeric material 104 are pressed up against the elastomeric feedthrough bushings 98 and 100 to effect a fluid tight seal around the feedthroughs.

The silicone rubber utilized in the preferred embodiment is type MDX4-4210 Silastic® brand silicone subdermal implant material. Silastic® is a registered trademark of The Dow Chemical Company for its series of unvulcanized organopolysiloxane elastomers.

The discount has heretofore been described only in reference to a hearing prothesis. It should be apparent, however, that the disconnect according to the invention has a far broader application. It is also suitable for use with brain stimulators, nerve stimulators and heart pacemakers, for example.

The terms and expressions which have been employed here are used as terms of description and not of limitations, and there is no intention, in the use of such terms and expressions, of excluding equivalents of the features shown and described, or portions thereof, it being recognized that various modifications are possible within the scope of the invention claimed.

What is claimed is:

1. A connector comprising a case, including a base member and a lid, the base member and lid being shaped to provide a cavity between them, a first contact pad of elastomeric material, a first set of electrical contacts embedded in the first contact pad, the contact pad being dimensioned to fit within the cavity, the contact pad being interposed between the lid and the base member, a second set of electrical contacts [carried by the lid] within the cavity, means for providing separate electrical connections through the case to the first and second sets of electrical contacts, and means for pressing the lid against the base member and the contact pad to exert a predetermined pressure on the pad, causing it to form a fluid tight seal around the first and second sets of electrical contacts, some of which are thereby placed in electrical contact with each other, *one of the first and second sets of electrical contacts being comprised of partially flattened metallic spheres.*

2. A connector as recited in claim 1 wherein the case is cylindrical and the first and second sets of electrical contact are each arranged in corresponding radial patterns.

3. A connector as recited in claim 1 wherein the first contact pad is comprised of silicone rubber reinforced with a mesh.

4. A connector as recited in claim 1 further comprising a second contact pad having a third set of electrical contacts arranged in a pattern to mate with the first set of electrical contacts, the second contact pad being made of an elastomeric material which is dimensioned to fit within the cavity, means for providing separate electrical connections through the case to the third set of electrical contacts, and wherein the second contact pad is interposed between the lid and the first contact pad.

5. A connector as recited in claim 4 wherein the second contact pad includes a fourth set of electrical contacts arranged in a pattern to mate with the second set of electrical contacts and means for providing separate electrical connections through the case to the fourth set of electrical contacts.

[6. A connector as recited in claims 1, 4 or 5 wherein one of the sets of electrical contacts are comprised of partially flattened metallic spheres.]

7. A connector as recited in claims 4 or 5 wherein the second contact pad is made of silicone rubber reinforced by mesh.

8. A connector as recited in claims 1 or 4 wherein the case is made of titanium.

9. In combination, a connector comprising a case, including a base member and a lid, the base member and lid being shaped to provide a cavity between them, a first contact pad of elastomeric material, a first set of electrical contacts embedded in the first contact pad, the contact pad being dimensioned to fit within the cavity, the contact pad being interposed between the lid and the base member, a second set of electrical contacts [carried by the lid] within the cavity, means for providing separate electrical connections through the case to the first and second sets of electrical contacts, means for pressing the lid against the base member and the contact pad to exert a predetermined pressure on the pad, causing it to form a fluid tight seal around the first and second sets of electrical contacts, some of which are thereby placed in electrical contact with each other, a second contact pad having a third set of electrical contacts arranged in a pattern to mate with the first set of electrical contacts, the second contact pad being made of an elastomeric material which is dimensioned to fit within the cavity, means for providing separate electrical connections through the case to the third set of electrical conacts, wherein the second contact pad is interposed between the lid and the first contact pad, a transcutaneous driving circuit receiver for a cochlear stimulating protheses, a cochlear stimulating electrode, a percutaneous plug, and wherein the driving circuit receiver is housed in the lid, and further including means for electrically connecting the second set of electrical contacts to the driving circuit receiver, means for electrically connecting the first set of electrical contacts to the cochlear stimulating electrode, and means for electrically connecting the percutaneous plug to the third set of electrical contacts.

10. The combination as recited in claim 9 wherein the second contact pad includes a fourth set of electrical contacts arranged in a pattern to mate with the second set of electrical contacts and further comprising means for electrically connecting the percutaneous plug to the fourth set of electrical contacts and means for providing separate electrical connections through the case to the fourth set of electrical contacts.

11. A connector as recited in claim 1 wherein the means for providing separate electrical connections through the case comprises electrical feedthroughs which pass through bores in the lid, bushings of elastomeric material surrounding the feedthroughs in the bores, and wherein the bushings, when the lid and base member are pressed together, are placed under pressure to form fluid tight seals around the feedthroughs.

12. A connector as recited in claim 1 or claim 11 wherein the base member is provided with a circumferential ridge, the lid is provided with a corresponding circumferential groove to mate with the base member ridge, an antennae coil disposed within the groove, an elastomeric material which pots the antennae coil in the groove, and further wherein the lid is provided with a second cavity for housing electronic circuitry, feedthrough means for electrically connecting the antennae to the electronic circuitry, and elastomeric bushings surrounding the feedthrough means, whereby, when the lid and base member are pressed together, a predetermined pressure is exerted on the elastomeric bushings through the elastomeric potting material in the groove to form a liquid tight seal around the feedthroughs.

*13. In a cochlear implant prosthesis including an implantable disconnect means for transmitting an electrical signal to at least one electrode implantable in the cochlea of a human ear, said disconnect means comprising*

*a base member,*

*a lid,*

*means for pressing said lid against said base member under a predetermined pressure to form a closed casing,*

*first electrical contact means mounted in said casing for transmitting said electrical signal to said electrode,*

*second electrical contact means mounted in said casing for receiving said electrical signal and transmitting it to said first electrical contact means,*

*elastomeric gasket means mounted in said casing for electrically isolating and forming a fluid tight seal around said first and second electrical contact means when said lid is pressed against said base member under said predetermined pressure, and*

*means mounted in said casing for receiving an external signal and for communicating said electrical signal to said second contact means in response to said external signal.*

*14. The cochlear implant prosthesis of claim 13 wherein said base member and said lid are shaped to provide a cavity therebetween, said gasket means disposed in said cavity.*

*15. The cochlear implant prosthesis of claim 13 wherein said first electrical contact means is mounted on an inner side of said base and said second electrical contact means is mounted in said gasket means and is maintained in direct contact with said first electrical contact means by said predetermined pressure.*

*16. The cochlear implant prosthesis of claim 15 further comprising third electrical contact means mounted on an inner side of said lid and maintained in direct contact with said second electrical contact means.*

*17. The cochlear implant prosthesis of claim 16 further comprising cable means for connecting said first electrical contact means to said electrode, said cable means extending through said case.*

*18. The cochlear implant prosthesis of claim 13 wherein said first and second electrical contact means comprise a plurality of circumferentially spaced first and second sets of contacts, respectively, and wherein the contacts of said first set of contacts are each maintained in electrical contact with a respective one of the contacts of said second set of contacts under said predetermined pressure.*

*19. The cochlear implant prosthesis of claim 18 wherein each of said first and second sets of contacts comprises radially spaced inner and outer sets of contacts.*

*20. The cochlear implant prosthesis of claim 18 wherein said gasket means comprises an elastomeric first gasket mounted on an inner side of said base, said first set of contacts embedded in said first gasket.*

*21. The cochlear implant prosthesis of claim 20 wherein said gasket means further comprises an elastomeric second gasket mounted between said first gasket and said lid, said second set of contacts embedded in said second gasket.*

*22. The cochlear implant prosthesis of claim 18 further comprising a plurality of electrodes embedded in an elastomeric material to form an electrode array adapted to be implantable in the cochlea of a human ear and cable means for connecting said electrodes to said first set of contacts, said cable means extending through said case.*

*23. A connector comprising a case, including a base member and a lid, the base member and lid being shaped to provide a cavity between them, a first contact pad of elastomeric material, a first set of electrical contacts embedded in the first contact pad, the contact pad being interposed between the lid and the base member, a second set of electrical contacts within the cavity, means for providing separate electrical connections through the case to the first and second sets of electrical contacts, means for pressing the lid against the base member and the contact pad to exert a predetermined pressure on the pad, causing it to form a fluid tight seal around the first and second sets of electrical contacts, some of which are thereby placed in electrical contact with each other, a second contact pad having a third set of electrical contacts arranged in a pattern to mate with the first set of electrical contacts, the second contact pad being made of elastomeric material which is dimensioned to fit within the cavity, and means for providing separate electrical connections through the case to the third set of electrical contacts, and wherein the second contact paid is interposed between the lid and the first contact pad.*

*24. In a cochlear implant prosthesis including an implantable disconnect means for transmitting an electrical signal to at least one electrode implantable in the cochlea of a human ear, said disconnect means comprising*

*a base member,*

*a lid,*

*means for pressing said lid against said base member under a predetermined pressure to form a closed casing,*

*first electrical contact means mounted in said casing for transmitting said electrical signal to said electrode,*

*second electrical contact means mounted in said casing for receiving said electrical signal and transmitting it to said first electrical contact means,*

*elastomeric gasket means mounted in said casing for electrically isolating and forming a fluid tight seal around said first and second electrical contact means when said lid is pressed against said base member under said predetermined pressure, said first and second electrical contact means comprising a plurality of circumferentially spaced first and second sets of contacts, respectively, and wherein the contacts of said first set of contacts are each maintained in electrical contact with a respective one of the contacts of said second set of contacts under said predetermined pressure.*

* * * * *